US009970050B2

(12) United States Patent
Schrader et al.

(10) Patent No.: US 9,970,050 B2
(45) Date of Patent: May 15, 2018

(54) HYDROLYSIS PROBES

(71) Applicant: LUMINEX CORPORATION, Austin, TX (US)

(72) Inventors: Brian Schrader, Austin, TX (US); Douglas F. Whitman, Round Rock, TX (US)

(73) Assignee: LUMINEX CORPORATION, Austin, TX (US)

( * ) Notice: Subject to any disclaimer, the term of this patent is extended or adjusted under 35 U.S.C. 154(b) by 291 days.

(21) Appl. No.: 14/602,846

(22) Filed: Jan. 22, 2015

(65) Prior Publication Data

US 2015/0133338 A1    May 14, 2015

Related U.S. Application Data

(63) Continuation of application No. 13/631,109, filed on Sep. 28, 2012, now abandoned.

(60) Provisional application No. 61/540,868, filed on Sep. 29, 2011.

(51) Int. Cl.
| | | |
|---|---|---|
| *C12Q 1/68* | (2018.01) | |
| *C12P 19/34* | (2006.01) | |
| *C07H 21/04* | (2006.01) | |

(52) U.S. Cl.
CPC ......... *C12Q 1/6823* (2013.01); *C12Q 1/6818* (2013.01)

(58) Field of Classification Search
None
See application file for complete search history.

(56) References Cited

U.S. PATENT DOCUMENTS

| | | | |
|---|---|---|---|
| 4,284,412 A | 8/1981 | Hansen et al. | |
| 4,498,766 A | 2/1985 | Unterleitner | |
| 4,661,913 A | 4/1987 | Wu et al. | |
| 4,714,682 A | 12/1987 | Schwartz | |
| 4,767,206 A | 8/1988 | Schwartz | |
| 4,774,189 A | 9/1988 | Schwartz | |
| 4,857,451 A | 8/1989 | Schwartz | |
| 4,942,124 A | 7/1990 | Church | |
| 4,989,977 A | 2/1991 | North, Jr. | |
| 5,160,974 A | 11/1992 | Siegel et al. | |
| 5,210,015 A * | 5/1993 | Gelfand ................. | C07H 21/00 435/18 |
| 5,478,722 A | 12/1995 | Caldwell | |
| 5,487,972 A | 1/1996 | Gelfand et al. | |
| 5,538,848 A | 7/1996 | Livak et al. | |
| 5,654,413 A | 8/1997 | Brenner | |
| 5,656,493 A | 8/1997 | Mullis et al. | |
| 5,716,784 A | 2/1998 | Di Cesare | |
| 5,736,330 A | 4/1998 | Fulton | |
| 5,837,832 A | 11/1998 | Chee et al. | |
| 5,837,860 A | 11/1998 | Anderson et al. | |
| 5,981,180 A | 11/1999 | Chandler et al. | |
| 5,994,056 A | 11/1999 | Higuchi | |
| 6,030,787 A | 2/2000 | Livak et al. | |
| 6,046,807 A | 4/2000 | Chandler | |
| 6,057,107 A | 5/2000 | Fulton | |
| 6,103,463 A | 8/2000 | Chetverin et al. | |
| 6,139,800 A | 10/2000 | Chandler | |
| 6,174,670 B1 | 1/2001 | Wittwer et al. | |
| 6,268,222 B1 | 7/2001 | Chandler et al. | |
| 6,322,971 B1 | 11/2001 | Chetverin et al. | |
| 6,366,354 B1 | 4/2002 | Chandler | |
| 6,411,904 B1 | 6/2002 | Chandler | |
| 6,449,562 B1 | 9/2002 | Chandler et al. | |
| 6,514,295 B1 | 2/2003 | Chandler et al. | |
| 6,524,793 B1 | 2/2003 | Chandler et al. | |
| 6,528,165 B2 | 3/2003 | Chandler | |
| 6,592,822 B1 | 7/2003 | Chandler | |
| 6,939,720 B2 | 9/2005 | Chandler et al. | |
| 7,205,105 B2 | 4/2007 | Afonina et al. | |
| 7,226,737 B2 | 6/2007 | Pancoska et al. | |
| 7,645,868 B2 | 1/2010 | Kobler et al. | |
| 7,955,802 B2 | 6/2011 | Whitman et al. | |
| 2005/0191625 A1 | 9/2005 | Kobler et al. | |
| 2008/0128597 A1 | 6/2008 | Smith et al. | |
| 2008/0241838 A1 | 10/2008 | Scaboo et al. | |

(Continued)

FOREIGN PATENT DOCUMENTS

| | | |
|---|---|---|
| CN | 101657548 | 2/2010 |
| WO | WO 89/09284 | 10/1989 |

(Continued)

OTHER PUBLICATIONS

"Viruses" (Wikipedia.com, accessed Nov. 24, 2012).*
"How many species of bacteria are there" (wisegeek.com; accessed Sep. 23, 2011).*
"Plant," (Wikipedia.com; accessed Mar. 8, 2013).*
"Mammal," (Wikipedia.com; accessed Sep. 22, 2011).*
"Viruses," Wikipedia.com, accessed Nov. 24, 2012.*
"How many species of bacteria are there," Wisegeek.com; accessed Sep. 23, 2011.*
"Plant," Wikipedia.com; accessed Mar. 8, 2013.*
"Mammal," Wikipedia.com; accessed Sep. 22, 2011.*
"Murinae," Wikipedia.com, accessed Mar. 18, 2013.*
"List of sequenced bacterial genomes," Wikipedia.com; accessed Jan. 24, 2014.*

(Continued)

*Primary Examiner* — Bradley L Sisson
(74) *Attorney, Agent, or Firm* — Parker Highlander PLLC

(57) ABSTRACT

Methods and compositions for the detection and quantification of nucleic acids are provided. In one embodiment, a sample is contacted with a primer complementary to a first region of a target nucleic acid and a probe complementary to a second region of the target nucleic acid downstream of the first region under conditions suitable for hybridization of the target nucleic acid with the primer and the probe. The probe in this embodiment comprises a fluorophore and is attached to a solid support. The hybridized probe is cleaved with a nucleic acid polymerase having exonuclease activity to release the reporter from the solid support. The presence of the target nucleic acid is then detected and optionally quantified by detecting a decrease in signal from the reporter on the solid support.

18 Claims, 3 Drawing Sheets

(56) References Cited

U.S. PATENT DOCUMENTS

| | | | |
|---|---|---|---|
| 2008/0305481 A1 | 12/2008 | Whitman et al. |
| 2009/0148849 A1 | 6/2009 | Galvan-Goldman et al. |
| 2010/0203572 A1 | 8/2010 | Lehmann et al. |
| 2010/0330574 A1 | 12/2010 | Whitman et al. |
| 2013/0085078 A1 | 4/2013 | Schrader et al. |
| 2013/0252827 A1 | 9/2013 | Chun |
| 2014/0045716 A1 | 2/2014 | Scaboo et al. |
| 2014/0242586 A1 | 8/2014 | Whitman et al. |
| 2014/0378327 A1 | 12/2014 | Whitman et al. |

FOREIGN PATENT DOCUMENTS

| | | |
|---|---|---|
| WO | WO 93/017126 | 9/1993 |
| WO | WO 97/031256 | 8/1997 |
| WO | WO 01/61034 | 8/2001 |
| WO | WO 2014/205083 | 12/2014 |

OTHER PUBLICATIONS

Office Action, issued in Chinese Application No. 201280048305.9, dated Apr. 3, 2015.
"How many species of bacteria are there?" wisegeek.com, accessed on Sep. 23, 2011.
"List of sequenced bacterial genomes," Wikipedia.com, accessed Jan. 24, 2014.
"Mammal," Wikipedia.com, accessed on Sep. 22, 2011.
"Murinae," WIkipedia.com, accessed on Mar. 18, 2013.
"Plant," Wikipedia.com, accessed on Mar. 8, 2013.
"Viruses," Wikipedia.com, accessed on Nov. 24, 2012.
Fodor et al., "Light-directed, spatially addressable parallel chemical synthesis," *Science*, 251:767-773, 1991.
Holmstrom et al., "A highly sensitive and fast nonradioactive method for detection of polymerase chain reaction products," *Anal. Biochem.*, 209:278-283, 1993.
Mueller et al, "Ligation-mediated PCR for genomic sequencing and footprints," In: Current Protocols in Mol. Biol., Unit 15.3, Frederick M. Ausubel et al.,Eds., John Wiley & Sons, Inc. 1993.
Newton et al., "The production of PCR products with 5' single-stranded tails using primers that incorporate novel phosphoradmidite intermediates ," *Nucleic Acids Research*, 21:1155-1162, 1993.
Office Action, issued in U.S. Appl. No. 13/631,109, dated Apr. 8, 2013.
Office Action, issued in U.S. Appl. No. 13/631;109, dated Feb. 4, 2014.
Office Action, issued in U.S. Appl. No. 13/631,109, dated Oct. 23, 2014.
PCT International Search Report and Written Opinion issued in International application No. PCT/US2012/057985, dated Feb. 12, 2013.
Pease et al., "Light-generated oligonucleotide arrays for rapid DNA sequence analysis," *Proc. Natl. Acad. Sci. USA*, 91:5022-5026, 1994.
Peyret et al., "Nearest-neighbor thermodynamics and NMR of DNA sequences with Internal A•A, C•C, G•G, and T•T mismatches," *Biochemistry*, 38:3468-3477, 1999.
Rasmussen et al. "Covalent immobilization of DNA onto polystyrene microwells: The molecules are only bound at the 5' end," *Anal. Biochem.*, 198:138-142, 1991.
Rödiger et al., "A Highly Versatile Microscope Imaging Technology Platform for the Multiplex Real-Time Detection of Biomolecules and Autoimmune Antibodies," *Adv Biochem Eng Biotechnol* 133:35-74, 2013.
Running et al., "A procedure for productive coupling of synthetic oligonucleotides to polystyrene microtitier wells for hybridization capture," *BioTechniques*, 8 :276-277, 1990.
Sommer and Tautz, "Minimal homology requirements for PCT primers" *Nucleic Acids Research*, 17:6749, 1989.
Extended Search Report and Opinion issued in European Application No. 12836978.2, dated Mar. 19, 2015.

\* cited by examiner

Template/amplification
= MFI decrease

No Template/No amplification
= high MFI

SEQUENCE LISTING

<160> NUMBER OF SEQ ID NOS: 4

<210> SEQ ID NO 1
<211> LENGTH: 27
<212> TYPE: DNA
<213> ORGANISM: Artificial Sequence
<220> FEATURE:
<223> OTHER INFORMATION: Synthetic primer
<220> FEATURE:
<221> NAME/KEY: 5AmMC12
<222> LOCATION: (1)..(1)
<220> FEATURE:
<221> NAME/KEY: 3Cy3Sp
<222> LOCATION: (27)..(27)

<400> SEQUENCE: 1
cagctgttcg taataatggc ggtggtc                                    27

<210> SEQ ID NO 2
<211> LENGTH: 24
<212> TYPE: DNA
<213> ORGANISM: Artificial Sequence
<220> FEATURE:
<223> OTHER INFORMATION: Synthetic primer
<220> FEATURE:
<221> NAME/KEY: 5AmMC12
<222> LOCATION: (1)..(1)
<220> FEATURE:
<221> NAME/KEY: 3Cy3Sp
<222> LOCATION: (24)..(24)

<400> SEQUENCE: 2
gattgtaaga tttgataaag tgta                                       24

<210> SEQ ID NO 3
<211> LENGTH: 21
<212> TYPE: DNA
<213> ORGANISM: Artificial Sequence
<220> FEATURE:
<223> OTHER INFORMATION: Synthetic primer

<400> SEQUENCE: 3
tcagcagttg aagggacaga t                                          21

<210> SEQ ID NO 4
<211> LENGTH: 22
<212> TYPE: DNA

```
<213> ORGANISM: Artificial Sequence
<220> FEATURE:
<223> OTHER INFORMATION: Synthetic primer

<400> SEQUENCE: 4
ccagaacaat gaatggttaa gg                                              22
```

HYDROLYSIS PROBES

This application is a continuation of U.S. application Ser. No. 13/631,109, filed Sep. 28, 2012, which claims priority to U.S. Provisional Patent Application Ser. No. 61/540,868, filed Sep. 29, 2011. The entirety of the above-referenced disclosure is incorporated by reference.

BACKGROUND OF THE INVENTION

1. Field of the Invention

The present invention relates generally to the field of molecular biology. More particularly, it concerns the detection and quantification of nucleic acids.

2. Description of Related Art

Polymerase chain reaction (PCR) is a molecular biology technique commonly used in medical and biological research labs for a variety of tasks, such as the detection of hereditary diseases, the identification of genetic fingerprints, the diagnosis of infectious diseases, the cloning of genes, paternity testing, and DNA computing. PCR has been accepted by molecular biologists as the method of choice for nucleic acid detection because of its unparalleled amplification and precision capability. DNA detection is typically performed at the end-point, or plateau phase of the PCR reaction, making it difficult to quantify the starting template. Real-time PCR or kinetic PCR advances the capability of end-point PCR analysis by recording the amplicon concentration as the reaction progresses. Amplicon concentration is most often recorded via a fluorescent signal change associated with the amplified target. Real-time PCR is also advantageous over end-point detection in that contamination is limited because it can be performed in a closed system. Other advantages include greater sensitivity, dynamic range, speed, and fewer processes required.

Several assay chemistries have been used in real-time PCR detection methods. These assay chemistries include using double-stranded DNA binding dyes, dual-labeled oligonucleotides, such as hairpin primers, and hairpin probes. Other chemistries include exonuclease based probes such as hydrolysis probes. Various PCR and real-time PCR methods are disclosed in U.S. Pat. Nos. 5,656,493; 5,994,056; 6,174,670; 5,716,784; 6,030,787; 6,174,670, and 7,955,802, which are incorporated herein by reference.

A drawback of many real-time PCR technologies is limited multiplexing capability. Real-time PCR technologies that use reporter fluorochromes that are free in solution require a spectrally distinct fluorochrome for each assay within a multiplex reaction. For example, a multiplex reaction designed to detect 4 target sequences would require an instrument capable of distinguishing 4 different free floating fluorochromes by spectral differentiation, not including controls. These requirements not only limit the practical multiplexing capability, but also increase costs since such instruments typically require multiple lasers and filters.

SUMMARY OF THE INVENTION

In certain embodiments, methods of detecting nucleic acids are provided. In one embodiment, the present invention provides a method for detecting a target nucleic acid in a sample, comprising: (a) contacting the sample with a first target-specific primer complementary to a first region on a first strand of the target nucleic acid, and a target-specific probe complementary to a second region on the first strand of the target nucleic acid downstream of the first region under conditions suitable for hybridization of the target nucleic acid with the target-specific primer and the target-specific probe, wherein the target-specific probe comprises a reporter and is attached to a solid support; (b) cleaving the hybridized target-specific probe with a nucleic acid polymerase having exonuclease activity to release the reporter from the solid support; and (c) detecting the target nucleic acid by detecting a change in signal from the reporter on the solid support. This method may be performed to detect a single target or additional primers and probes may be included to detect multiple different target nucleic acids in a multiplex assay. For example, in one embodiment the method further comprises: (a) contacting the sample with at least a second target-specific primer complementary to a first region on a first strand of a second target nucleic acid, and at least a second target-specific probe complementary to a second region on the first strand of the second target nucleic acid downstream of the first region under conditions suitable for hybridization of the second target nucleic acid with the second target-specific primer and the second target-specific probe, wherein the second target-specific probe comprises a second reporter and is attached to a second solid support; (b) cleaving the second hybridized target-specific probe with the nucleic acid polymerase having exonuclease activity to release the second reporter from the second solid support; and (c) detecting the second target nucleic acid by detecting a change in signal from the second reporter on the second solid support.

The first solid support and the second solid support may be spatially discrete locations on the same solid support, such as spatially discrete locations on a planar array, or the first solid support may be physically separate from the second solid support, such as with a bead array. In a multiplexed method, the reporters attached to the different target-specific probes may be the same because the different target-specific probes can be distinguished by the solid support(s) to which they are attached. In some embodiments, however, two or more different reporters are used.

Another embodiment provides a multiplex method for detecting the presence or absence of a plurality of target nucleic acids in a sample, comprising: (a) contacting the sample with a plurality of primer/probe pairs, each primer/probe pair comprising a target-specific primer complementary to a first region on a first strand of one of the plurality of target nucleic acids, and a target-specific probe complementary to a second region on the first strand of one of the plurality of target nucleic acids downstream of the first region under conditions suitable for hybridization of the target nucleic acid with the first target-specific primer and the target-specific probe, wherein the target-specific probe comprises a reporter and is attached to a solid support; (b) cleaving the hybridized target-specific probes with a nucleic acid polymerase having exonuclease activity to release the reporters from the solid support; and (c) detecting a signal from the reporters on the solid support, whereby a change in the signal indicates the presence of a target nucleic acid. In certain aspects, each different target-specific probe of the plurality of primer/probe pairs is attached to a spatially discrete location on one solid. In other aspects, each different target-specific probe of the plurality of primer/probe pairs is attached to a different solid support. In some embodiments the method may further comprise contacting the sample with a plurality of different second target-specific primers complementary to a region on a second strand of the plurality of target nucleic acids, and performing multiple polymerase chain reaction cycles. The multiple polymerase chain reaction cycles may be performed with or without a wash step to remove free-floating reporters between cycles.

The change in the signal may be a decrease or an increase in signal depending on the type of reporter employed. For example, if the reporter is a fluorophore, the change in signal that will be observed in the presence of the target nucleic acid is a decrease in fluorescent signal. On the other hand, if the reporter is a fluorphore and quencher pair, the separation of the fluorophore from the quencher results in an increase in a fluorescent signal when the target nucleic acid is present.

The terms "upstream" and "downstream" are used herein in relation to the synthesis of the nascent strand that is primed by a target-specific primer. Thus, for example, a target-specific probe hybridized to a region of the target nucleic acid that is "downstream" of the region of the target nucleic acid to which the primer is hybridized is located 3' of the primer and will be in the path of a polymerase extending the primer in a 5' to 3' direction.

In certain aspects, the method further comprises contacting the sample with a second target-specific primer complementary to a region on a second strand of the target nucleic acid. The first target-specific primer and the second target-specific primer are oriented on opposite strands of the target nucleic acid such that the region of the target nucleic acid can be amplified by PCR. In certain aspects, the method comprises performing multiple amplification cycles. A typical amplification cycle has three phases: a denaturing phase, a primer annealing phase, and a primer extension phase, with each phase being carried out at a different temperature. A 2-stage PCR also may be performed in which only two temperatures are used for each cycle; e.g., 95° C. and 60° C. Thus, in certain aspects the method further comprises repeatedly hybridizing the target nucleic acid with the target-specific primers and the target-specific probe, extending the target-specific primers with the nucleic acid polymerase having exonuclease activity such that extension of the first target-specific primer results in the cleavage of the hybridized target-specific probe and release the reporter from the solid support, and detecting the change in signal from the reporter on the solid support. In certain embodiments amplification cycles are repeated at least until the change in the signal is distinguishable from background noise. Although, if a particular target nucleic acid is not present in the sample, then the change in signal should not be distinguishable from background noise regardless of the number of cycles performed. The inclusion of appropriate positive and negative controls in the reaction can assist in determining that a particular target nucleic acid is not present in the sample. A person of ordinary skill in the art will know how to select the appropriate positive and negative controls for a particular assay.

In some embodiments, a signal from the reporter on the solid support is detected prior to extending the target-specific primers with the nucleic acid polymerase having exonuclease activity to cleave the hybridized target-specific probe and release the reporter from the solid support. In some embodiments, the change in signal from the reporter on the solid support comprises detecting the signal before and after performing the multiple polymerase chain reaction cycles. In some embodiments, the change in signal from the reporter on the solid support comprises detecting the signal between two or more amplification cycles. In other embodiments, the change in signal from the reporter on the solid support comprises detecting the signal only after performing the multiple polymerase chain reaction cycles.

In one embodiment, the methods disclosed herein provide an end-point detection of the presence or absence of a target nucleic acid by relating the change in signal from the reporter on the solid support to a reference signal from a reporter on a non-hybridizing probe attached to a solid support. In particular embodiment, the detected signal from the reporter on the solid support is compared to a predetermined ratio of the signal of the reporter on the solid support to a reference signal from a reporter on a non-hybridizing probe attached to a solid support. Determining that the ratio has changed would indicate the presence of the target nucleic acid in the assay. An advantage of this approach is that it can be performed without requiring multiple images (e.g., one image before amplification and one image after amplification). In certain aspects, the predetermined ratio is stored in a computer-readable medium and accessed by software analyzing data relating to the signals from the reporter molecules. A "non-hybridizing probe" is a probe that has a sequence that is not expected to hybridize to any other nucleic acids present in the assay under assay conditions.

In another embodiment, the present inventions provides a method for detecting a target nucleic acid in a sample, comprising: (a) contacting the sample with a first target-specific primer complementary to a first region on a first strand of the target nucleic acid, and a target-specific probe complementary to a second region on the first strand of the target nucleic acid downstream of the first region under conditions suitable for hybridization of the target nucleic acid with the target-specific primer and the target-specific probe, wherein the target-specific probe comprises a tag at its 5' or 3' end and a reporter; (b) cleaving the hybridized target-specific probe with a nucleic acid polymerase having exonuclease activity to release the reporter from the tag; (c) hybridizing the tag to its complementary anti-tag immobilized on a solid support; and (d) detecting the target nucleic acid by detecting a decrease in signal from the reporter on the solid support. In certain aspects, the method further comprises hybridizing the target-specific probe to the anti-tag immobilized on the solid support prior to cleaving the hybridized target-specific probe and releasing the reporter molecule from the tag; and detecting a signal from the reporter on the solid support. This method may be performed to detect a single target or additional primers and probes may be included to detect multiple different target nucleic acids in a multiplex assay. For example, in one embodiment the method further comprises: (a) contacting the sample with a second target-specific primer complementary to a first region on a first strand of a second target nucleic acid, and a second target-specific probe complementary to a second region on the first strand of the second target nucleic acid downstream of the first region under conditions suitable for hybridization of the second target nucleic acid with the second target-specific primer and the second target-specific probe, wherein the second target-specific probe comprises a second tag at its 5' or 3' end and a second reporter; (b) cleaving the second hybridized target-specific probe with the nucleic acid polymerase having exonuclease activity to release the second reporter from the second tag; (c) hybridizing the second tag to a complementary second anti-tag immobilized on a second solid support; and (c) detecting the second target nucleic acid by detecting a decrease in signal from the second reporter on the second solid support. The first solid support and the second solid support may be spatially discrete locations on the same solid support, such as spatially discrete locations on a planar array, or the first solid support may be physically separate from the second solid support, such as with a bead array. In a multiplexed method, the reporters attached to the different target-specific probes may be the same because the different target-specific probes can be distinguished by the solid support(s) to which they are attached. In some embodiments, however, two or more different reporters are used.

In some embodiments, the method further comprises contacting the sample with a second target-specific primer complementary to a region on a second strand of the target nucleic acid. The first target-specific primer and the second target-specific primer are oriented on opposite strands of the target nucleic acid such that the region of the target nucleic acid can be amplified by PCR. In certain aspects, the method comprises performing multiple amplification cycles. Thus, in certain aspects the method further comprises repeatedly hybridizing the target nucleic acid with the target-specific primers and the target-specific probe, extending the target-specific primers with the nucleic acid polymerase having exonuclease activity such that extension of the first target-specific primer results in the cleavage of the hybridized target-specific probe and release of the reporter, and detecting the decrease in signal from the reporter on the solid support at least until the change in the signal is distinguishable from background noise. In certain aspects, the change in signal from the reporter on the solid support after one or more amplification cycles is used to quantify the amount of the target nucleic acid in the sample. The tag may comprise isobases and/or nucleic acid analogs.

The target-specific primer and the target-specific probe may hybridize to adjacent or non-adjacent sequences on the target nucleic acid. Where the target-specific primer and the target-specific probe hybridize to adjacent sequence, the polymerase can cleave the target-specific probe without necessarily extending the target-specific primer. Thus, in certain aspects the methods may or may not comprise extending the target-specific primer with the nucleic acid polymerase having exonuclease activity.

In certain embodiments, one or more controls are included in the reaction. For example, in some embodiments a method for detecting a target nucleic acid in a sample may further comprising detecting a signal from a reporter on a non-hybridizing (i.e., negative control) probe attached to a solid support. The non-hybridizing probe may be attached to a spatially discrete location on the same solid support to which the target-specific probe is attached, attached to a different solid support than that to which the target-specific probe is attached, or otherwise distinguishable from the target-specific probe. In certain embodiments, the different solid supports are different encoded beads.

The target nucleic acid may be any sequence of interest. In some embodiments, the nucleic acid is a DNA. In some embodiments, the nucleic acid is an RNA. The sample containing the target nucleic acid may be any sample that contains nucleic acids. In certain aspects of the invention the sample is, for example, from a subject who is being screened for the presence or absence of one or more genetic mutations or polymorphisms. In another aspect of the invention the sample may be from a subject who is being tested for the presence or absence of a pathogen. Where the sample is obtained from a subject, it may be obtained by methods known to those in the art such as aspiration, biopsy, swabbing, venipuncture, spinal tap, fecal sample, or urine sample. In some aspects of the invention, the sample is an environmental sample such as a water, soil, or air sample. In other aspects of the invention, the sample is from a plant, bacteria, virus, fungi, protozoan, or metazoan. The term target nucleic acid encompasses both an unamplified sequence and amplicons thereof.

A primer is a nucleic acid that is capable of priming the synthesis of a nascent nucleic acid in a template-dependent process. A target-specific primer refers to a primer that has been designed to prime the synthesis of a particular target nucleic acid. A primer pair refers to two primers, commonly known as a forward primer and a reverse primer or as an upstream primer and a downstream primer, which are designed to amplify a target sequence between the binding sites of the two primers on a template nucleic acid molecule. In certain embodiments, the primer has a target-specific sequence that is between 10-40, 15-30, or 18-26 nucleotides in length. A probe is a nucleic acid that is capable of hybridizing to a complementary nucleic acid. A target-specific probe refers to a probe that has been designed to hybridize to a particular target nucleic acid. Probes present in the reaction may comprise a blocked 3' hydroxyl group to prevent extension of the probes by the polymerase. The 3' hydroxyl group may be blocked with, for example, a phosphate group, a 3' inverted dT, or a reporter. High stringency hybridization conditions may be selected that will only allow hybridization between sequences that are completely complementary.

Various aspects of the present invention use sets of complementary tag and anti-tag sequences. Which sequence in a complementary pair is called the "tag" and which is called the "anti-tag" is arbitrary. The tags and anti-tags are preferably non-cross hybridizing, i.e., each tag and anti-tag should hybridize only to its complementary partner, and not to other tags or anti-tags in the same reaction. Preferably, the tags and anti-tags also will not hybridize to other nucleic acids in the sample during a reaction. The tag and anti-tag sequences are also preferably designed to be isothermic, i.e., of similar optimal hybridization temperature, whereby all of the tag and anti-tag sequences in a multiplex reaction will have approximately the same Tm. The proper selection of non-cross hybridizing tag and anti-tag sequences is useful in assays, particularly assays in a highly parallel hybridization environment, that require stringent non-cross hybridizing behavior. In certain embodiments, the tag and anti-tag sequences are between 6 to 60, 8 to 50, 10 to 40, 10 to 20, 12 to 24, or 20 to 30 nucleotides in length. In some embodiments, the tag and anti-tag sequences are 12, 14, 16, or 24 nucleotides in length. A number of tag and tag complement (i.e., anti-tag) sequences are known in the art and may be used in the present invention. For example, U.S. Pat. No. 7,226,737, incorporated herein by reference, describes a set of 210 non-cross hybridizing tags and anti-tags. In addition, U.S. Pat. No. 7,645,868, incorporated herein by reference, discloses a family of 1168 tag sequences with a demonstrated ability to correctly hybridize to their complementary sequences with minimal cross hybridization. A "universal" tag or anti-tag refers to a tag or anti-tag that has the same sequence across all reactions in a multiplex reaction.

A reporter which may also be referred to as a labeling agent, is a molecule that facilitates the detection of another molecule (e.g., a nucleic acid) to which it is attached. Numerous reporter molecules that may be used to label nucleic acids are known. Direct reporter molecules include fluorophores, chromophores, and radiophores. Non-limiting examples of fluorophores include, a red fluorescent squarine dye such as 2,4-Bis[1,3,3-trimethyl-2-indolinylidenemethyl]cyclobutenediylium-1,3-dioxolate, an infrared dye such as 2,4 Bis[3,3-dimethyl-2-(1H-benz[e]indolinylidenemethyl)]cyclobutenediylium-1,3-dioxolate, or an orange fluorescent squarine dye such as 2,4-Bis[3,5-dimethyl-2-pyrrolyl]cyclobutenediylium-1,3-diololate. Additional non-limiting examples of fluorophores include quantum dots, Alexa Fluor® dyes, AMCA, BODIPY® 630/650, BODIPY® 650/665, BODIPY®-FL, BODIPY®-R6G, BODIPY®-TMR, BODIPY®-TRX, Cascade Blue®, CyDye™, including but not limited to Cy2™, Cy3™, and Cy5™, a DNA intercalating dye, 6-FAM™, Fluorescein, HEX™, 6-JOE, Oregon Green® 488, Oregon Green® 500, Oregon Green® 514, Pacific Blue™, REG, phycobilliproteins including, but not limited to, phycoerythrin and allophycocyanin, Rhodamine Green™, Rhodamine Red™, ROX™, TAMRA™, TET™, Tetramethylrhodamine, or Texas Red®. A signal amplification reagent, such as tyramide (PerkinElmer), may be used to enhance the fluorescence signal. Indirect reporter molecules include biotin, which must be bound to another molecule such as streptavidin-phycoerythrin for detection. Pairs of labels, such as fluorescence resonance energy transfer pairs or dye-quencher pairs, may also be employed.

In some embodiments, non-natural bases that differ from the naturally occurring bases (A, T, C, G, and U) in their hydrogen bonding pattern may be incorporated into the primers and probes described herein. One example are the isoC and isoG bases that hydrogen bond with each other, but not with natural bases. The incorporation of these non-natural bases in primers and/or probes is useful in reducing non-specific hybridization. Methods of using such non-natural bases to assay target nucleic acids are disclosed in U.S. Pat. No. 6,977,161, which is incorporated herein by reference. In one embodiment, at least one of the two target-specific primers used to amplify the target nucleic acid includes at least 1, 2, 3, or 4 non-natural bases, and the complementary non-natural base is included in the amplification reaction, such that the non-natural base(s) is included in the amplification product. In such an embodiment, a complementary non-natural base(s) is incorporated in the probe. The presence of complementary non-natural bases, such as isoC and isoG, in the probe and the target sequence will permit hybridization between these sequences but decrease non-specific hybridization with other sequences. In certain aspects of the invention, a solid support is used. A variety of solid supports for the immobilization of biomolecules are known. For example, the solid support may be nitrocellulose, nylon membrane, glass, activated quartz, activated glass, polyvinylidene difluoride (PVDF) membrane, polystyrene substrates, polyacrylamide-based substrate, other polymers, copolymers, or crosslinked polymers such as poly(vinyl chloride), poly(methyl methacrylate), poly(dimethyl siloxane), photopolymers (which contain photoreactive species such as nitrenes, carbenes and ketyl radicals capable of forming covalent links with target molecules). A solid support may be in the form of, for example, a bead (microsphere), a column, or a chip. Molecules immobilized on planar solid supports are typically identified by their spatial position on the support. Molecules immobilized on non-planar solid supports, such as particles or beads, are often identified by some form of encoding of the support, as discussed below. In some embodiments, a linker is placed between the target-specific probe or the anti-tag and the solid support to which it is attached.

Beads and particles may be encoded such that one subpopulation of beads or particles can be distinguished from another subpopulation. Encoding may be by a variety of techniques. For example, the beads may be fluorescently labeled with fluorescent dyes having different emission spectra and/or different signal intensities. In certain embodiments, the beads are Luminex MagPlex® microspheres or Luminex xMAP® microspheres. The size of the beads in a subpopulation may also be used to distinguish one subpopulation from another. Another method of modifying a bead is to incorporate a magnetically responsive substance, such as $Fe_3O_4$, into the structure. Paramagnetic and superparamagnetic microspheres have negligible magnetism in the absence of a magnetic field, but application of a magnetic field induces alignment of the magnetic domains in the microspheres, resulting in attraction of the microspheres to the field source. Combining fluorescent dyes, bead size, and/or magnetically responsive substances into the beads can further increase the number of different subpopulations of beads that can be created.

Detection of the target nucleic acid may be by a variety of techniques. In one aspect of the invention, the amplified target nucleic acids are detected using a flow cytometer. Flow cytometry is particularly well-suited where the solid support of the capture complex is a bead or other particle. In other aspects of the invention, detecting the amplified target nucleic acid comprises imaging the amplified target nucleic acid sequence bound to the capture complex in a static imaging system, such a bead array platform or a chip array platform.

The methods of the present invention may be used in multiplexed assays. In such multiplexed assays, the sample will typically comprise at least a second target nucleic acid sequence. In certain aspects of the invention, there are 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, 100, 120, 140, 160, 180, 200, 220, 240, 260, 280, 300, 400, 500, 600, 700, 800, 900, 1000, or any range derivable therein, target nucleic acid sequences in the sample. As mentioned above, a target nucleic acid sequence may be any sequence of interest. One target nucleic acid sequence may be in the same gene or a different gene as another target nucleic acid sequence, and the target nucleic acid sequences may or may not overlap. Of course, a target nucleic acid sequence need not be within a gene but may be within, for example, a non-coding region of DNA. In a multiplex assay where at least a second target nucleic acid to be amplified is present in a sample, at least a second discriminating primer or primer pair is included in the reaction.

The methods of detecting the nucleic acid may comprise repeatedly extending the primer along the template nucleic acid to amplify the sequence. The amplification may be qualitative, semi-quantitative, or quantitative. In certain embodiments, the amplification may be monitored in real time (e.g., real-time PCR). The amplification cycle can be repeated until the desired amount of amplification product is produced. Typically, the amplification cycle is repeated between about 10 to 40 times. For real-time PCR, detection of the amplification products will typically be done after each amplification cycle. Although in certain aspects of the invention, detection of the amplification products may be done after only a subset of the amplification cycles, such as after every second, third, fourth, or fifth amplification cycle. Detection may also be done such that as few as 2 or more amplification cycles are analyzed or detected.

In yet another embodiment, the present invention provides a method for detecting a target nucleic acid in a sample, comprising: (a) contacting the sample with a first target-specific primer complementary to a first region on a first strand of the target nucleic acid, and a target-specific probe complementary to a second region on the first strand of the target nucleic acid downstream of the first region under conditions suitable for hybridization of the target nucleic acid with the target-specific primer and the target-specific probe, wherein the target-specific probe comprises a fluorophore at its 5' or 3' end and a biotin at the end opposite the fluorphore; (b) extending the target-specific primer with a nucleic acid polymerase having exonuclease activity to cleave the hybridized target-specific probe and separate the fluorophore from the biotin; (c) removing the biotin from the sample; and (d) detecting the target nucleic acid by detecting a signal from the fluorophore. In some embodiments, removing biotin from the sample comprises contacting the sample with magnetic avidin coated beads to bind the biotin, and removing the biotin-bound magnetic avidin coated beads. In certain aspects, the method further comprises contacting the sample with a second target-specific primer complementary to a region on a second strand of the target nucleic acid. The method may further comprises performing multiple polymerase chain reaction cycles prior to removing the biotin from the sample.

In certain embodiments, methods of quantifying an amount of nucleic acids are provided. In one embodiment, a method for quantifying an amount of a target nucleic acid in a sample is provided which comprises: (a) amplifying the target nucleic acid in the presence of a nucleic acid polymerase having exonuclease activity, a target-specific primer pair, wherein the primer pair comprises a first primer complementary to a first region on a first strand of the target nucleic acid and a second primer complementary to a region on a second strand of the target nucleic acid, and a target-specific probe complementary to a second region on the first strand of the target nucleic acid downstream of the first region, wherein the target-specific probe comprises a reporter and is attached to a solid support, and further wherein the nucleic acid polymerase cleaves the target-specific probe and releases the reporter from the solid support when extending the first target-specific primer along the target nucleic acid; (c) detecting a first signal from the reporter on the solid support at a first time and a second signal from the reporter on the solid support at a second time; and (d) correlating a change in signal with the amount of nucleic acid in the sample. In some embodiments, the method further comprises detecting at least a $3^{rd}$, $4^{th}$, $5^{th}$, $6^{th}$, $7^{th}$, $8^{th}$, $9^{th}$, $10^{th}$, $11^{th}$, $12^{th}$, $13^{th}$, $14^{th}$, $15^{th}$, $16^{th}$, $17^{th}$, $18^{th}$, $19^{th}$, $20^{th}$, $21^{st}$, $22^{nd}$, $23^{rd}$, $24^{th}$, $25^{th}$, $26^{th}$, $27^{th}$, $28^{th}$, $29^{th}$, $30^{th}$, $31^{st}$, $32^{nd}$, $33^{rd}$, $34^{th}$, $35^{th}$, $36^{th}$, $37^{th}$, $38^{th}$, $39^{th}$, or $40^{th}$ signal from the reporter on the solid support at a $3^{rd}$, $4^{th}$, $5^{th}$, $6^{th}$, $7^{th}$, $8^{th}$, $9^{th}$, $10^{th}$, $11^{th}$, $12^{th}$, $13^{th}$, $14^{th}$, $15^{th}$, $16^{th}$, $17^{th}$, $18^{th}$, $19^{th}$, $20^{th}$, $21^{st}$, $22^{nd}$, $23^{rd}$, $24^{th}$, $25^{th}$, $26^{th}$, $27^{th}$, $28^{th}$, $29^{th}$, $30^{th}$, $31^{st}$, $32^{nd}$, $33^{rd}$, $34^{th}$, $35^{th}$, $36^{th}$, $37^{th}$, $38^{th}$, $39^{th}$, or $40^{th}$ time. In certain aspects, the method comprises detecting a signal from the reporter on the solid support prior to extending the target-specific primers with the nucleic acid polymerase having exonuclease activity to cleave the hybridized target-specific probe and release the reporter from the solid support. In some embodiments, the method comprises quantifying an amount of a plurality of different target nucleic acids in the sample.

In another embodiment, a method for quantifying an amount of a target nucleic acid in a sample is provided, which comprises: (a) amplifying the target nucleic acid in the presence of a nucleic acid polymerase having exonuclease activity, a target-specific primer complementary to a first region of the target nucleic acid, and a target-specific probe complementary to a second region of the target nucleic acid downstream of the first region under conditions suitable for hybridization of the target nucleic acid with the target-specific primer and the target-specific probe, wherein the target-specific probe comprises a tag at its 5' or 3' end and a reporter, and further wherein the nucleic acid polymerase cleaves the target-specific probe and releases the reporter from the solid support when extending the target-specific primer along the target nucleic acid; (c) detecting a first signal from the reporter on the solid support at a first time and a second time from the reporter on the solid support at a second time; and (d) correlating a change between the first signal and the second signal with the amount of nucleic acid in the sample. In some embodiments, the method further comprises detecting at least a $3^{rd}$, $4^{th}$, $5^{th}$, $6^{th}$, $7^{th}$, $8^{th}$, $9^{th}$, $10^{th}$, $11^{th}$, $12^{th}$, $13^{th}$, $14^{th}$, $15^{th}$, $16^{th}$, $17^{th}$, $18^{th}$, $19^{th}$, $20^{th}$, $21^{st}$, $22^{nd}$, $23^{rd}$, $24^{th}$, $25^{th}$, $26^{th}$, $27^{th}$, $28^{th}$, $29^{th}$, $30^{th}$, $31^{st}$, $32^{nd}$, $33^{rd}$, $34^{th}$, $35^{th}$, $36^{th}$, $37^{th}$, $38^{th}$, $39^{th}$, or $40^{th}$ signal from the reporter on the solid support at a $3^{rd}$, $4^{th}$, $5^{th}$, $6^{th}$, $7^{th}$, $8^{th}$, $9^{th}$, $10^{th}$, $11^{th}$, $12^{th}$, $13^{th}$, $14^{th}$, $15^{th}$, $16^{th}$, $17^{th}$, $18^{th}$, $19^{th}$, $20^{th}$, $21^{st}$, $22^{nd}$, $23^{rd}$, $24^{th}$, $25^{th}$, $26^{th}$, $27^{th}$, $28^{th}$, $29^{th}$, $30^{th}$, $31^{st}$, $32^{nd}$, $33^{rd}$, $34^{th}$, $35^{th}$, $36^{th}$, $37^{th}$, $38^{th}$, $39^{th}$, or $40^{th}$ time. In certain aspects, the method comprises detecting a signal from the reporter on the solid support prior to extending the target-specific primer with the nucleic acid polymerase having exonuclease activity to cleave the hybridized target-specific probe and release the reporter from the solid support. In some embodiments, the method comprises quantifying an amount of a plurality of different target nucleic acids in the sample.

In one embodiment, the present invention provides a method for quantifying an amount of a target nucleic acid in a sample, comprising: (a) amplifying the target nucleic acid in the presence of a nucleic acid polymerase having exonuclease activity, a target-specific primer pair, wherein the primer pair comprises a first primer complementary to a first region on a first strand of the target nucleic acid and a second primer complementary to a region on a second strand of the target nucleic acid, and a target-specific probe complementary to a second region on the first strand of the target nucleic acid downstream of the first region under conditions suitable for hybridization of the target nucleic acid with the target-specific primer pair and the target-specific probe, wherein the target-specific probe comprises a fluorophore at its 5' or 3' end and a biotin at the end opposite the fluorphore, and further wherein the template-dependent nucleic acid polymerase cleaves the hybridized target-specific probe when extending the first primer along the target nucleic acid thereby separating the fluorophore from the biotin; (c) removing the biotin from the sample; (d) detecting a first signal from the fluorophore on the solid support at a first time and a second signal from the fluorophore at a second time; (e) correlating a change in signal with the amount of nucleic acid in the sample. In some embodiments, the method further comprises detecting at least a $3^{rd}$, $4^{th}$, $5^{th}$, $6^{th}$, $7^{th}$, $8^{th}$, $9^{th}$, $10^{th}$, $11^{th}$, $12^{th}$, $13^{th}$, $14^{th}$, $15^{th}$, $16^{th}$, $17^{th}$, $18^{th}$, $19^{th}$, $20^{th}$, $21^{st}$, $22^{nd}$, $23^{rd}$, $24^{th}$, $25^{th}$, $26^{th}$, $27^{th}$, $28^{th}$, $29^{th}$, $30^{th}$, $31^{st}$, $32^{nd}$, $33^{rd}$, $34^{th}$, $35^{th}$, $36^{th}$, $37^{th}$, $38^{th}$, $39^{th}$, or $40^{th}$ signal from the fluorophore on the solid support at a $3^{rd}$, $4^{th}$, $5^{th}$, $6^{th}$, $7^{th}$, $8^{th}$, $9^{th}$, $10^{th}$, $11^{th}$, $12^{th}$, $13^{th}$, $14^{th}$, $15^{th}$, $16^{th}$, $17^{th}$, $18^{th}$, $19^{th}$, $20^{th}$, $21^{st}$, $22^{nd}$, $23^{rd}$, $24^{th}$, $25^{th}$, $26^{th}$, $27^{th}$, $28^{th}$, $29^{th}$, $30^{th}$, $31^{st}$, $32^{nd}$, $33^{rd}$, $34^{th}$, $35^{th}$, $36^{th}$, $37^{th}$, $38^{th}$, $39^{th}$, or $40^{th}$ time. In certain aspects, the method comprises detecting a signal from the fluorophore prior to extending the target-specific primer with the nucleic acid polymerase having exonuclease activity. In some embodiments, the method comprises quantifying an amount of a plurality of different target nucleic acids in the sample.

In another embodiment, the present invention provides a method for quantifying an amount of a target nucleic acid in a sample, comprising: (a) amplifying the target nucleic acid in the presence of a nucleic acid polymerase having exonuclease activity, a target-specific primer pair comprising a first primer complementary to a first region on a first strand of the target nucleic acid and a second primer complementary to a region on a second strand of the target nucleic acid, and a target-specific probe complementary to a second region on the first strand of the target nucleic acid downstream of the first region under conditions suitable for hybridization of the target nucleic acid with the target-specific primer pair and the target-specific probe, wherein the target-specific probe comprises a tag and a fluorophore at its 5' or 3' end and a biotin at the end opposite the tag and the fluorphore, and further wherein the nucleic acid polymerase cleaves the hybridized target-specific probe when extending the target-specific primer along the target nucleic acid thereby separating the fluorophore from the biotin; (b) removing the biotin from the sample; (c) hybridizing the tag sequence to a complementary anti-tag sequence on a solid support; (d) detecting a fluorescent signal from the fluorophore on the solid support; (e) correlating the fluorescent signal with the amount of nucleic acid in the sample.

In quantitative PCR the threshold cycle (Ct) reflects the cycle number at which the fluorescence generated within a reaction crosses the threshold. It is inversely correlated to the logarithm of the initial copy number. The determination of the Ct value for each reaction is related to the baseline, background, and threshold set by the software. In some qPCR methods, a passive reference dye is used and the signal from the fluorescent reporter is divided by the signal from the reference dye to account for variability in the reaction medium. This calculation gives the normalized reporter signal (Rn). The baseline refers to the initial cycles in PCR in which there is little expected change in fluorescent signal (usually cycles 3 to 15) This baseline can be used to determine the background for each reaction. In a multiwell reaction plate, several baselines from multiple wells may be used to determine the 'baseline fluorescence' across the plate. There are many ways to use data analysis to determine when target amplification is above the background signal (crosses the threshold). Rn can be subtracted by the background signal to give ΔRn. Other supplements to data analysis that are typically employed in qPCR may be applied to the present invention. Namely, the use of endogenous and exogenous controls, housekeeping genes, standard curves, internal positive controls, no amplification controls, reverse transcription controls, nontreated controls, extraction controls, time point zeros, healthy individual controls, and negative and positive controls. These may be used in the present invention in order to perform Comparative Ct analysis ("relative quantitation") or standard curve analysis ("absolute quantitation"), the Pfaffl method, end-point quantitation, qualitative results, allelic discrimination, etc. Accounting for amplification efficiency or amplification rate may be performed by a number of methods including but not limited to: Dilution method, fluorescence increase in exponential phase, Sigmoidal or logistic curve fit, etc. The threshold may be determined by a number of methods including but not limited to the second derivative maximum method, or by a multiple of standard deviations above background, etc. Endpoint quantitative analysis could be performed by a number of methods including but not limited to: relative, absolute, competitive and comparative.

In the methods described herein, the variability in signal from well to well is not as high as in conventional bulk fluorescence measurement qPCR. In bulk fluorescent PCR, some changes in signal can be related to volume differences in each well. In certain embodiments of the present invention, volume differences will not change fluorescence attached on a solid support, and a passive bulk fluid reference dye is not needed. As multiple images are taken of spectrally identifiable particles, changes in focus and light intensity within or between imaging chambers may cause variability in signal. This can be normalized by calibration particles or passive reference particles. Calibration particles can be used to focus and optimize the light intensity or detector settings for each imaging chamber before analysis of the reaction. They can also be mixed with each reaction to normalize signal from image to image. A calibration particle is generally internally dyed with a known amount of classification dye as well as reporter dye. A passive reference particle may be used to normalize signal by subtracting or dividing from the target specific probes. A passive reference particle is generally externally dyed with probes that are designed to not hybridize or interact with any other portions of target nucleic acid in the reaction. Other particles may include those with no reporter dye, internal or external can be used to normalize for changes in bulk fluorescence which may affect the measured signal on each particle in the reaction. Sections of the imaging chamber that do not contain beads may also be used to normalize signal.

There are many ways in which the data analysis can be done. Below is an illustrative example of one method for performing data analysis for relative quantitation of mRNA. After calibration of the imaging chamber with calibration particles, one or more regions of passive reference particles and one or more regions of target specific particles as well as one or more regions specific for an endogenous control or housekeeping gene are included in an imaging chamber capable of thermal cycling. Each of the particle types is spectrally identifiable by internal classification dyes, which divide them into regions. At least 30 particles of each region are included in the reaction. The first 10 cycles of the reaction are imaged during the annealing or extension phase of the PCR cycle. A median fluorescent intensity (MFI) value is determined by taking the median of the at least 30 particles of each region. These first 10 cycles represent the baseline. The MFI of the target specific and endogenous control particles is divided by the MFI of the passive reference particle (Rn). The average Rn from the baseline is used to subtract from subsequent images as the reaction proceeds (ΔRn). A threshold is determined by taking the standard deviation (SD) of the Rn for each region and multiplying it by 10. When the ΔRn exceeds 10 SD of the baseline a Ct is recorded for each particle region. These Ct values may then be analyzed by normalizing the target specific regions to the housekeeping or endogenous control regions. This normalization is typically done by taking the difference of the Ct of the target specific region by that of the endogenous control (ΔCt). Next, if two samples are to be compared (test sample vs. control sample, or disease vs. healthy sample) then the 'delta-delta Ct' method could be used without correcting for efficiency (R= $2^{-[\Delta Ct\ sample - \Delta Ct\ control]}$).

Amplification efficiency may be determined either by direct or indirect methods known to those in the art and can be used to correct quantification data. Direct methods can include determining the amplification efficiency by the dilution method or by a measurement of the relative fluorescence in the exponential phase. Other indirect methods may include fitting amplification curves to a mathematical model such as sigmoidal, logistic or exponential curve fitting. In certain embodiments the quantitation of target nucleic acids is achieved using digital PCR (dPCR). In this approach the sample is partitioned so that individual nucleic acid molecules contained in the sample are localized in many separate regions, such as in individual wells in microwell plates, in the dispersed phase of an emulsion, or arrays of nucleic acid binding surfaces. Each partition will contain 0 or 1 molecule, providing a negative or positive reaction, respectively. Unlike conventional PCR, dPCR is not dependent on the number of amplification cycles to determine the initial amount of the target nucleic acid in the sample. Accordingly, dPCR eliminates the reliance on exponential data to quantify target nucleic acids and provides absolute quantification.

The present invention also provides compositions and kits for use in any of the disclosed methods. For example, in one embodiment a composition may comprise (a) at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, 100, 120, 140, 160, 180, 200, 220, 240, 260, 280, 300, 400, 500, 600, 700, 800, 900, 1000, or any range derivable therein, different primer-probe sets, wherein each primer-probe set comprises: (i) a first primer complementary to a first region on a first strand of a target nucleic acid, (ii) a second primer complementary to a region on a second strand of the target nucleic acid, and (iii) a labeled target-specific probe covalently attached to a distinguishably encoded particle, wherein the labeled target-specific probe is capable of specifically hybridizing to a second region on the first strand of the target nucleic acid, wherein the second region is downstream of the first region. The composition may further comprise a polymerase with 5' exonuclease activity. In some embodiments, the composition further comprises one or more negative-control (i.e., passive reference) probes covalently attached to a distinguishably encoded particle. Negative-control probes are probes that are designed such that they do not specifically hybridize to any nucleic acid expected to be in a given sample. In some embodiments, the composition further comprises one or more positive-control probes covalently attached to a distinguishably encoded particle. Positive-control probes are probes that are designed such that they specifically hybridize to a nucleic acid expected to be in a given sample.

In another embodiment, a kit is provided that may comprise (a) at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, 100, 120, 140, 160, 180, 200, 220, 240, 260, 280, 300, 400, 500, 600, 700, 800, 900, 1000, or any range derivable therein, different primer-probe sets, wherein each primer-probe set comprises: (i) a first primer complementary to a first region on a first strand of a target nucleic acid, (ii) a second primer complementary to a region on a second strand of the target nucleic acid, and (iii) a labeled target-specific probe covalently attached to a distinguishably encoded particle, wherein the labeled target-specific probe is capable of specifically hybridizing to a second region on the first strand of the target nucleic acid, wherein the second region is downstream of the first region. The kit may further comprise a polymerase with 5' exonuclease activity. In some embodiments, the kit further comprises one or more negative-control probes covalently attached to a distinguishably encoded particle. In some embodiments, the kit further comprises one or more positive-control probes covalently attached to a distinguishably encoded particle. Components of the kit may be provided in the same container or in separate containers packaged together. In certain embodiments the kit is an infectious disease kit, and primer-probe pairs are designed to amplify target sequences from pathogens (e.g., bacteria, viruses). In other embodiments the kit is an gene expression profiling kit, and primer-probe pairs are designed to amplify target sequences from various expressed gene sequences.

As used herein, "hybridization," "hybridizes" or "capable of hybridizing" is understood to mean the forming of a double or triple stranded molecule or a molecule with partial double or triple stranded nature. The term "anneal" as used herein is synonymous with "hybridize." As used herein "stringent conditions" or "high stringency" are those conditions that allow hybridization between or within one or more nucleic acid strands containing complementary sequences, but preclude hybridization of non-complementary sequences. Such conditions are well known to those of ordinary skill in the art, and are preferred for applications requiring high selectivity. Stringent conditions may comprise low salt and/or high temperature conditions. It is understood that the temperature and ionic strength of a desired stringency are determined in part by the length of the particular nucleic acids, the length and nucleobase content of the target sequences, the charge composition of the nucleic acids, and to the presence or concentration of formamide, tetramethylammonium chloride or other solvents in a hybridization mixture.

It is contemplated that any method or composition described herein can be implemented with respect to any other method or composition described herein.

The terms "comprise" (and any form of comprise, such as "comprises" and "comprising"), "have" (and any form of have, such as "has" and "having"), "contain" (and any form of contain, such as "contains" and "containing"), and "include" (and any form of include, such as "includes" and "including") are open-ended linking verbs. As a result, a method, composition, kit, or system that "comprises," "has," "contains," or "includes" one or more recited steps or elements possesses those recited steps or elements, but is not limited to possessing only those steps or elements; it may possess (i.e., cover) elements or steps that are not recited. Likewise, an element of a method, composition, kit, or system that "comprises," "has," "contains," or "includes" one or more recited features possesses those features, but is not limited to possessing only those features; it may possess features that are not recited.

Any embodiment of any of the present methods, composition, kit, and systems may consist of or consist essentially of—rather than comprise/include/contain/have—the described steps and/or features. Thus, in any of the claims, the term "consisting of" or "consisting essentially of" may be substituted for any of the open-ended linking verbs recited above, in order to change the scope of a given claim from what it would otherwise be using the open-ended linking verb.

The use of the term "or" in the claims is used to mean "and/or" unless explicitly indicated to refer to alternatives only or the alternatives are mutually exclusive, although the disclosure supports a definition that refers to only alternatives and "and/or."

Throughout this application, the term "about" is used to indicate that a value includes the standard deviation of error for the device or method being employed to determine the value.

Following long-standing patent law, the words "a" and "an," when used in conjunction with the word "comprising" in the claims or specification, denotes one or more, unless specifically noted.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 2A shows a target nucleic acid (amplicon) to which a primer and target-specific probe having a biotin at one end and a tag sequence at the other end are hybridized. In FIG. 2B, a polymerase is synthesizing a new strand primed by the primer. The polymerase encounters and cleaves the target-specific probe separating the biotin from the tag (FIG. 2B). FIG. 2C shows a tag cleaved from a target-specific probe that has hybridized to a complementary tag attached to a spectrally encoded bead. FIG. 2D shows an uncleaved target-specific probe in which the tag hybridized to a complementary tag attached to a spectrally encoded bead.

DESCRIPTION OF ILLUSTRATIVE EMBODIMENTS

A. Hydrolysis Probes

Certain aspects of the present invention employ hydrolysis probes for the detection of nucleic acids. Hydrolysis probes take advantage of the 5' exonuclease activity of some polymerases. During the extension or elongation phase of a PCR reaction, a polymerase, such as Taq polymerase, uses an upstream primer as a binding site and then extends. The hydrolysis probe is then cleaved during polymerase extension at its 5' end by the 5'-exonuclease activity of the polymerase.

However, the process of cleaving the 5' end of the probe need not require amplification or extension of the target sequence (see, e.g., U.S. Pat. No. 5,487,972, incorporated herein by reference). This is accomplished by placing the probe in close proximity to the upstream primer on the target sequence such that binding of the nucleic acid polymerase to the 3' end of the primer automatically puts the polymerase in contact with the 5' end of the probe. Because polymerization is not required to bring the polymerase into position to cleave the probe, this may be referred to as "polymerization-independent cleavage." In this manner, sequential rounds of annealing and subsequent probe hydrolysis can occur, resulting in a significant amount of signal generation in the absence of polymerization.

The TaqMan® assay (see, e.g., U.S. Pat. No. 5,210,015, incorporated herein by reference) is an example of a hydrolysis-probe based assay. In the TaqMan® assay, hydrolysis probes are typically labeled with a reporter on the 5' end and a quencher on the 3' end. When the reporter and quencher are fixed onto the same probe, they are forced to remain in close proximity. This proximity effectively quenches the reporter signal, even when the probe is hybridized to the target sequence. The hydrolysis probes are cleaved during polymerase extension at their 5' end by the 5'-exonuclease activity of Taq. When this occurs, the reporter fluorophore is released from the probe, and subsequently, is no longer in close proximity to the quencher. This produces a perpetual increase in reporter signal with each extension phase as the PCR reaction continues cycling. In order to achieve maximal signal with each cycle, hydrolysis probes are often designed with a Tm that is roughly 10° C. higher than the primers in the reaction. Uses of the real-time hydrolysis probe reaction are also described in U.S. Pat. Nos. 5,538,848 and 7,205,105, both of which are incorporated by references.

Figure 1:
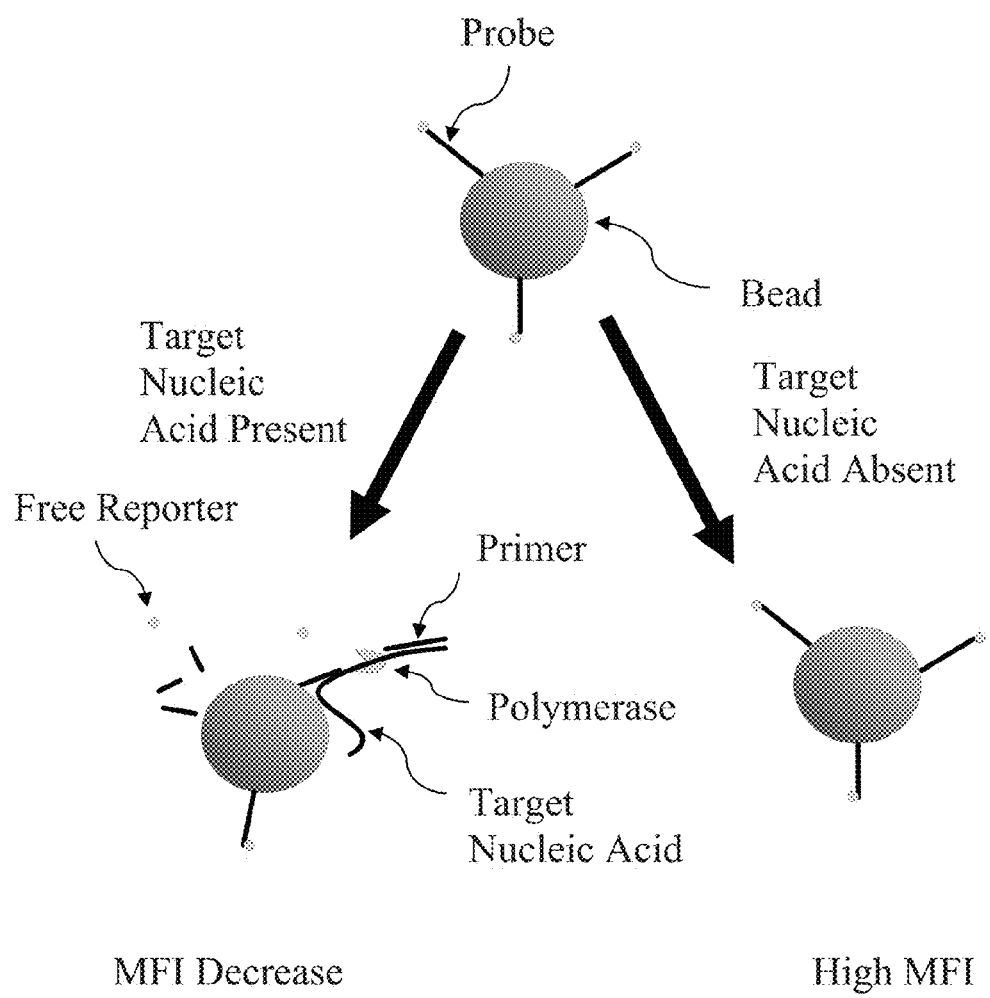
FIG. 1 shows a plurality of target-specific probes attached to a spectrally identifiable bead at one end and having a fluorophore at their opposite ends.

FIG. 1 illustrates one embodiment of the present invention. A target specific probe is attached to a spectrally identifiable bead at one end and a fluorophore at the opposite end. The flourophore would be cleaved due to exonuclease activity of the polymerase when another amplified sequence has bound to a target strand upstream of the probe/fluor/bead complex. In this method, a decrease in signal would be observed when the target nucleic acid is present in the reaction. Other beads that are designed to be non-hybridizing can be used to measure the background signal, which may change over time due to the effect of temperature on the fluorophores. This particular method is advantageous for real-time quantitative assays, because the fluorescence is only on the beads and not in solution at the beginning of the reaction. The total fluorescence that ends up in solution can be controlled by the number of amplicons present in the multiplex, and the number of beads placed in the solution. This method is also advantageous because it does not require an end-point hybridization step or subsequent labeling of the beads. Additionally, there is no waiting for a hybridization event on the beads prior to each data point acquisition. This method provides several advantages over the TaqMan® assay described above. For example, quenching molecules are not needed because bulk-fluorescence measurements do not have to be performed. Furthermore, the spectrally identifiable beads allow one to perform highly multiplexed reactions, including highly multiplexed real-time PCR reactions. While this embodiment has been described using fluorophores and spectrally encoded beads, other labels and solid supports could be used.

Figure 2A:
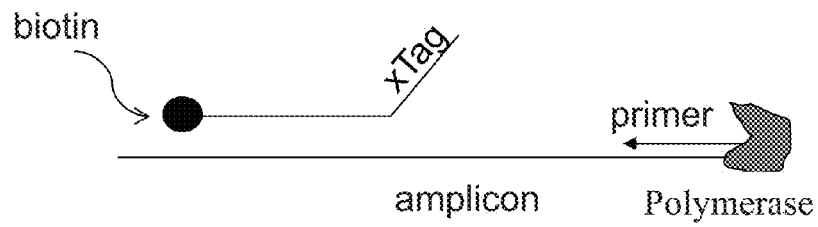
FIGS. 2A-2D.
Figure 2B:
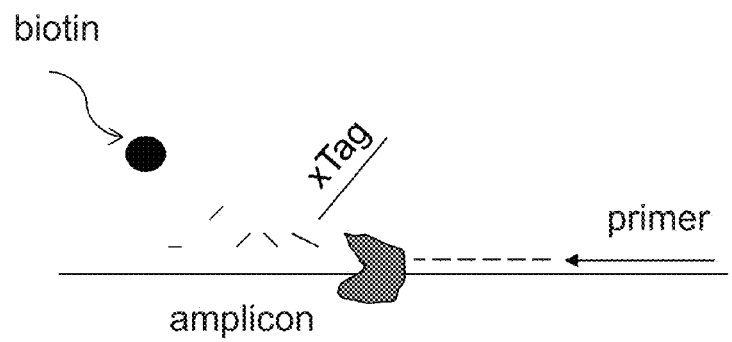
Figure 2C:
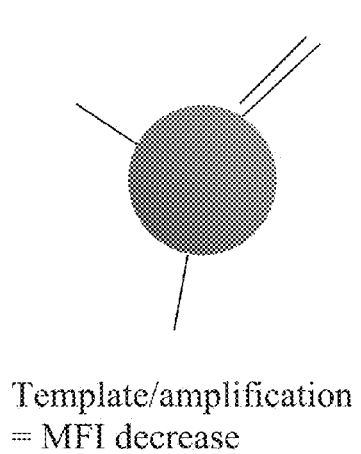
Figure 2D:
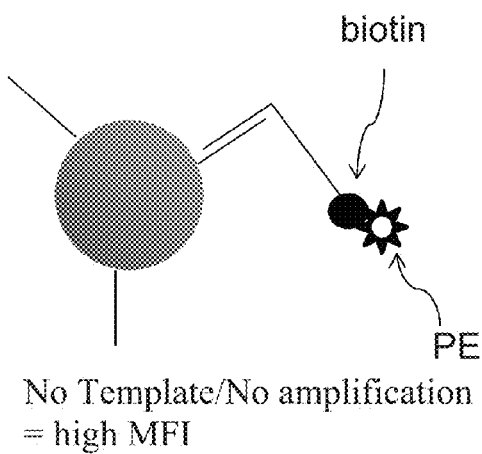

FIGS. 2A-2D illustrates another embodiment of the present invention. In FIG. 2A, a primer and target-specific probe having a biotin at one end and a tag sequence at the other end are hybridized to a target nucleic acid. The biotin and the tag may be reversed so that the tag is at either the 3' or 5' end of the probe. The primer primes the synthesis of a new strand by a polymerase. When the polymerase encounters the target-specific probe, it cleaves the probe separating the biotin from the tag (FIG. 2B). FIGS. 2C and 2D show the tags hybridized to complementary tags on spectrally encoded beads. In FIG. 2C, the tag has been cleaved from the target-specific probe by the polymerase. In FIG. 2D, however, the target-specific probe was not cleaved. Consequently, a biotin-PE complex can be formed resulting in a detectable signal. Thus, a decrease in signal would be observed when the target nucleic acid is present in the reaction. In this embodiment, the biotin may be substituted with any fluorochrome.

In another embodiment, a fluorophore may be attached at either the 3' end or 5' end of the probe and a biotin may be attached at the opposite end. In this configuration, the biotin would be cleaved from the probe by the exonuclease activity of the polymerase. Then, a biotin clean up step is used with an excess of magnetic avidin coated beads. If a probe/fluor/biotin complex has not been cleaved due to a lack of target, then the entire complex will be removed from the reaction in the clean-up step. If cleavage has occurred, the biotin will be released from the tag/fluorophore and only the biotin will be removed from the reaction during the clean-up step. Thus, an increase in signal on the hybridization beads is observed if a target nucleic acid was present during amplification.

B. PCR

The polymerase chain reaction (PCR) is a technique widely used in molecular biology to amplify a piece of DNA by in vitro enzymatic replication. Typically, PCR applications employ a heat-stable DNA polymerase, such as Taq polymerase. This DNA polymerase enzymatically assembles a new DNA strand from nucleotides (dNTPs) using single-stranded DNA as template and DNA primers to initiate DNA synthesis. A basic PCR reaction requires several components and reagents including: a DNA template that contains the target sequence to be amplified; one or more primers, which are complementary to the DNA regions at the 5' and 3' ends of the target sequence; a DNA polymerase (e.g., Taq polymerase) that preferably has a temperature optimum at around 70° C.; deoxynucleotide triphosphates (dNTPs); a buffer solution providing a suitable chemical environment for optimum activity and stability of the DNA polymerase; divalent cations, typically magnesium ions ($Mg^{2+}$); and monovalent cation potassium ions.

The majority of PCR methods use thermal cycling to subject the PCR sample to a defined series of temperature steps. Each cycle typically has 2 or 3 discrete temperature steps. The cycling is often preceded by a single temperature step ("initiation") at a high temperature (>90° C.), and followed by one or two temperature steps at the end for final product extension ("final extension") or brief storage ("final hold"). The temperatures used and the length of time they are applied in each cycle depend on a variety of parameters. These include the enzyme used for DNA synthesis, the concentration of divalent ions and dNTPs in the reaction, and the melting temperature (Tm) of the primers. Commonly used temperatures for the various steps in PCR methods are: initialization step—94-96° C.; denaturation step—94-98° C.; annealing step—50-65° C.; extension/elongation step—70-74° C.; final elongation—70-74° C.; final hold—4-10° C.

Real-time polymerase chain reaction, also called quantitative real time polymerase chain reaction (qPCR) or kinetic polymerase chain reaction, is used to amplify and simultaneously quantify a targeted DNA molecule. It enables both detection and quantification (as absolute number of copies or relative amount when normalized to DNA input or additional normalizing genes) of a specific sequence in a DNA sample. Real-time PCR may be combined with reverse transcription polymerase chain reaction to quantify low abundance RNAs. Relative concentrations of DNA present during the exponential phase of real-time PCR are determined by plotting fluorescence against cycle number on a logarithmic scale. Amounts of DNA may then be determined by comparing the results to a standard curve produced by real-time PCR of serial dilutions of a known amount of DNA.

Digital PCR (dPCR) involves partitioning the sample such that individual nucleic acid molecules contained in the sample are localized in many separate regions, such as in individual wells in microwell plates, in the dispersed phase of an emulsion, or arrays of nucleic acid binding surfaces. Each partition will contain 0 or 1 molecule, providing a negative or positive reaction, respectively. Unlike conventional PCR, dPCR is not dependent on the number of amplification cycles to determine the initial amount of the target nucleic acid in the sample. Accordingly, dPCR eliminates the reliance on exponential data to quantify target nucleic acids and provides absolute quantification.

Multiplex-PCR and multiplex real-time PCR use of multiple, unique primer sets within a single PCR reaction to produce amplicons of different DNA sequences. By targeting multiple genes at once, additional information may be gained from a single test run that otherwise would require several times the reagents and more time to perform. Annealing temperatures for each of the primer sets should be optimized to work within a single reaction.

C. Complementary Tags

Some embodiments of the present invention employ complementary tag sequences (i.e., tags and anti-tags) in the primers and/or probes. The proper selection of non-hybridizing tag and anti-tag sequences is useful in assays, particularly assays in a highly parallel hybridization environment, that require stringent non-cross hybridizing behavior.

Certain thermodynamic properties of forming nucleic acid hybrids are considered in the design of tag and anti-tag sequences. The temperature at which oligonucleotides form duplexes with their complementary sequences known as the $T_m$ (the temperature at which 50% of the nucleic acid duplex is dissociated) varies according to a number of sequence dependent properties including the hydrogen bonding energies of the canonical pairs A-T and G-C (reflected in GC or base composition), stacking free energy and, to a lesser extent, nearest neighbor interactions. These energies vary widely among oligonucleotides that are typically used in hybridization assays. For example, hybridization of two probe sequences composed of 24 nucleotides, one with a 40% GC content and the other with a 60% GC content, with its complementary target under standard conditions theoretically may have a 10° C. difference in melting temperature (Mueller et al., 1993). Problems in hybridization occur when the hybrids are allowed to form under hybridization conditions that include a single hybridization temperature that is not optimal for correct hybridization of all oligonucleotide sequences of a set. Mismatch hybridization of non-complementary probes can occur, forming duplexes with measurable mismatch stability (Santalucia et al., 1999). Mismatching of duplexes in a particular set of oligonucleotides can occur under hybridization conditions where the mismatch results in a decrease in duplex stability that results in a higher $T_m$ than the least stable correct duplex of that particular set. For example, if hybridization is carried out under conditions that favor the AT-rich perfect match duplex sequence, the possibility exists for hybridizing a GC-rich duplex sequence that contains a mismatched base having a melting temperature that is still above the correctly formed AT-rich duplex. Therefore, design of families of oligonucleotide sequences that can be used in multiplexed hybridization reactions must include consideration for the thermodynamic properties of oligonucleotides and duplex formation that will reduce or eliminate cross hybridization behavior within the designed oligonucleotide set.

There are a number of different approaches for selecting tag and anti-tag sequences for use in multiplexed hybridization assays. The selection of sequences that can be used as zip codes or tags in an addressable array has been described in the patent literature in an approach taken by Brenner and co-workers (U.S. Pat. No. 5,654,413, incorporated herein by reference). Chetverin et al. (WO 93/17126, U.S. Pat. Nos. 6,103,463 and 6,322,971, incorporated herein by reference) discloses sectioned, binary oligonucleotide arrays to sort and survey nucleic acids. These arrays have a constant nucleotide sequence attached to an adjacent variable nucleotide sequence, both bound to a solid support by a covalent linking moiety. Parameters used in the design of tags based on subunits are discussed in Barany et al. (WO 9731256, incorporated herein by reference). A multiplex sequencing method has been described in U.S. Pat. No. 4,942,124, incorporated herein by reference. This method uses at least two vectors that differ from each other at a tag sequence.

U.S. Pat. No. 7,226,737, incorporated herein by reference, describes a set of 210 non-cross hybridizing tags and anti-tags. U.S. Published Application No. 2005/0191625, incorporated herein by reference, discloses a family of 1168 tag sequences with a demonstrated ability to correctly hybridize to their complementary sequences with minimal cross hybridization. U.S. Publication No. 2009/0148849, incorporated herein by reference, describes the use of tags, anti-tags, and capture complexes in the amplification of nucleic acid sequences.

A population of oligonucleotide tag or anti-tag sequences may be conjugated to a population of primers or other polynucleotide sequences in several different ways including, but not limited to, direct chemical synthesis, chemical coupling, ligation, amplification, and the like. Sequence tags that have been synthesized with target specific primer sequences can be used for enzymatic extension of the primer on the target for example in PCR amplification. A population of oligonucleotide tag or anti-tag sequences may be conjugated to a solid support by, for example, surface chemistries on the surface of the support.

D. Solid Supports

In certain embodiments, the probes and/or primers may be attached to a solid support. Such solid supports may be, for example, microspheres (i.e., beads) or other particles such as microparticles, gold or other metal nanoparticles, quantum dots, or nanodots. In certain aspects, the particles may be magnetic, paramagnetic, or super paramagnetic. Examples of microspheres, beads, and particles are illustrated in U.S. Pat. No. 5,736,330 to Fulton, U.S. Pat. No. 5,981,180 to Chandler et al., U.S. Pat. No. 6,057,107 to Fulton, U.S. Pat. No. 6,268,222 to Chandler et al., U.S. Pat. No. 6,449,562 to Chandler et al., U.S. Pat. No. 6,514,295 to Chandler et al., U.S. Pat. No. 6,524,793 to Chandler et al., and U.S. Pat. No. 6,528,165 to Chandler, which are incorporated by reference herein.

The particles may be encoded with a label. In certain embodiments, the present invention is used in conjunction with Luminex® xMAP® and MagPlex™ technologies. The Luminex xMAP technology allows the detection of nucleic acid products immobilized on fluorescently encoded microspheres. By dyeing microspheres with 10 different intensities of each of two spectrally distinct fluorochromes, 100 fluorescently distinct populations of microspheres are produced. These individual populations (sets) can represent individual detection sequences and the magnitude of hybridization on each set can be detected individually. The magnitude of the hybridization reaction is measured using a third reporter, which is typically a third spectrally distinct fluorophore. In embodiments in which a labeled hydrolysis probe is attached to the microsphere, hybridization and hydrolysis of the probe results in a decrease in signal from the third reporter. As both the microspheres and the reporter molecules are labeled, digital signal processing allows the translation of signals into real-time, quantitative data for each reaction. The Luminex technology is described, for example, in U.S. Pat. Nos. 5,736,330, 5,981,180, and 6,057,107, all of which are specifically incorporated by reference. Luminex® MagPlex™ microspheres are superparamagnetic microspheres that are fluorescently encoded using the xMAP® technology discussed above. The microspheres contain surface carboxyl groups for covalent attachment of ligands (or biomolecules).

Alternatively, the solid support may be a planar array such as a gene chip or microarray (see, e.g., Pease et al., 1994; Fodor et al., 1991). The identity of nucleic acids on a planar array is typically determined by it spatial location on the array. Microsphere based assays may also be analyzed on bead array platforms. In general, bead array platforms image beads and analytes distributed on a substantially planar array. In this way, imaging of bead arrays is similar to the gene chips discussed above. However, in contrast to gene chips where the analyte is typically identified by its spatial position on the array, bead arrays typically identify the analyte by the encoded microsphere to which it is bound.

The ability to directly synthesize on or attach polynucleotide probes to solid substrates is well known in the art. See U.S. Pat. Nos. 5,837,832 and 5,837,860, both of which are incorporated by reference. A variety of methods have been utilized to either permanently or removably attach the probes to the substrate. Exemplary methods include: the immobilization of biotinylated nucleic acid molecules to avidin/streptavidin coated supports (Holmstrom, 1993), the direct covalent attachment of short, 5'-phosphorylated primers to chemically modified polystyrene plates (Rasmussen et al., 1991), or the precoating of the polystyrene or glass solid phases with poly-L-Lys or poly L-Lys, Phe, followed by the covalent attachment of either amino- or sulfhydryl-modified oligonucleotides using bi-functional crosslinking reagents (Running et al., 1990; Newton et al., 1993). Numerous materials may be used as solid supports, including reinforced nitrocellulose membrane, activated quartz, activated glass, polyvinylidene difluoride (PVDF) membrane, polystyrene substrates, polyacrylamide-based substrate, other polymers such as poly(vinyl chloride), poly(methyl methacrylate), poly(dimethyl siloxane), photopolymers (which contain photoreactive species such as nitrenes, carbenes and ketyl radicals capable of forming covalent links with target molecules.

E. Detection

Various aspects of the present invention relate to the direct or indirect detection of one or more target nucleic acids by detecting an increase or decrease in a signal. The detection techniques employed will depend on the type of reporter and platform (e.g., spectrally encoded beads, microarray, etc.). Flow cytometry, for example, is particularly useful in the analysis of microsphere based assays. Flow cytometry involves the separation of cells or other particles, such as microspheres, in a liquid sample. Generally, the purpose of flow cytometry is to analyze the separated particles for one or more characteristics. The basic steps of flow cytometry involve the direction of a fluid sample through an apparatus such that a liquid stream passes through a sensing region. The particles should pass one at a time by the sensor and are categorized based on size, refraction, light scattering, opacity, roughness, shape, fluorescence, etc.

In the context of the Luminex xMAP® system, flow cytometry can be used for simultaneous sequence identification and hybridization quantification. Internal dyes in the microspheres are detected by flow cytometry and used to identify the specific nucleic acid sequence to which a microsphere is coupled. The label on the target nucleic acid molecule or probe is also detected by flow cytometry and used to determine hybridization to the microsphere.

Methods of flow cytometry are well known in the art and are described, for example, in U.S. patents, all of which are specifically incorporated by reference. U.S. Pat. Nos. 5,981,180, 4,284,412; 4,989,977; 4,498,766; 5,478,722; 4,857,451; 4,774,189; 4,767,206; 4,714,682; 5,160,974; and 4,661,913. The measurements described herein may include image processing for analyzing one or more images of particles to determine one or more characteristics of the particles such as numerical values representing the magnitude of fluorescence emission of the particles at multiple detection wavelengths. Subsequent processing of the one or more characteristics of the particles such as using one or more of the numerical values to determine a token ID representing the multiplex subset to which the particles belong and/or a reporter value representing a presence and/or a quantity of analyte bound to the surface of the particles can be performed according to the methods described in U.S. Pat. No. 5,736,330 to Fulton, U.S. Pat. No. 5,981,180 to Chandler et al., U.S. Pat. No. 6,449,562 to Chandler et al., U.S. Pat. No. 6,524,793 to Chandler et al., U.S. Pat. No. 6,592,822 to Chandler, and U.S. Pat. No. 6,939,720 to Chandler et al., which are incorporated by reference herein.

In one example, techniques described in U.S. Pat. No. 5,981,180 to Chandler et al. may be used with the fluorescent measurements described herein in a multiplexing scheme in which the particles are classified into subsets for analysis of multiple analytes in a single sample. Additional examples of systems that may be configured as described herein (e.g., by inclusion of an embodiment of an illumination subsystem described herein) are illustrated in U.S. Pat. No. 5,981,180 to Chandler et al., U.S. Pat. No. 6,046,807 to Chandler, U.S. Pat. No. 6,139,800 to Chandler, U.S. Pat. No. 6,366,354 to Chandler, U.S. Pat. No. 6,411,904 to Chandler, U.S. Pat. No. 6,449,562 to Chandler et al., and U.S. Pat. No. 6,524,793 to Chandler et al., which are incorporated by reference herein.

Microspheres may also be analyzed on array platforms that image beads and analytes distributed on a substantially planar array. In this way, imaging of bead arrays is similar to imaging of gene chips. However, in contrast to gene chips where the analyte is identified by its spatial position (i.e., x, y coordinate) on the array, bead arrays typically identify the analyte by the encoded microsphere to which it is bound. Examples of commercially available bead array systems include Luminex's MAGPIX®, and Illumina's BeadXpress™ Reader and BeadStation 500™. Once beads are in a planar layer, they can be identified by their "coding" (either in the form of embedded dyes, or other methods that create unique signals for each bead type). Following or preceding the resolution of the "code" of the bead, the signal can be measured and these two measurements coupled to determine the hybridization of a particular nucleic acid to the bead.

F. Kits

The present invention also provides kits containing components for use with the amplification and detection methods disclosed herein. Any of the components disclosed here in may be combined in a kit. In certain embodiments the kits comprise a plurality of primers for priming amplification of a plurality of nucleic acid targets, and a plurality of probes complementary to the plurality of nucleic acid targets. In some embodiments, the probes are immobilized on a solid support(s). In one embodiment, a plurality of probes are attached to a plurality of encoded magnetic beads such that the identity of each probe is known from the encoded magnetic bead on which it is immobilized. In certain embodiments, the kit also comprises a labeling agent. In certain embodiments the kits comprise probes that are not attached to a solid support. In some embodiments the kit comprises an imaging chamber, which may be a disposable imaging chamber, for use in an imaging system.

The kits will generally include at least one vial, test tube, flask, bottle, syringe or other container, into which a component may be placed, and preferably, suitably aliquoted. Where there is more than one component in the kit, the kit also will generally contain a second, third or other additional containers into which the additional components may be separately placed. However, various combinations of components may be comprised in a container. The kits of the present invention also will typically include packaging for containing the various containers in close confinement for commercial sale. Such packaging may include cardboard or injection or blow molded plastic packaging into which the desired containers are retained.

A kit may also include instructions for employing the kit components. Instructions may include variations that can be implemented.

G. Examples

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Luminex MagPlex® Microspheres were coupled to amine-modified oligonucleotide probes according to the manufacturer's instructions.

Microsphere region 25 was coupled to a probe specific for *Staphylococcus Epidermidis*:

(SEQ ID NO: 1)
5'- /5AmMC12/CAG CTG TTC GTA ATA ATG GCG GTG GTC/

3Cy3Sp/-3'

Microsphere region 54 was coupled to a probe that was designed to not hybridize to *Staphylococcus Epidermidis*:

(SEQ ID NO: 2)
5'-/5AmMC12/GAT TGT AAG ATT TGA TAA AGT GTA/

3Cy3Sp/-3'

Next a PCR Master mix was made for each reaction including:

| | |
|---|---|
| 2x TaqMan ® Master Mix (Applied Biosystems) | 12.5 µL |
| Water | 5.7 µL |
| 50 mM MgCl$_2$ | 2.0 µL |
| 20x Primer Mix | 1.3 µL |
| 2500 beads/µL per region | 1.0 µL |

The 20× Primer Mix contained the following ratios per µL:

| | |
|---|---|
| TE pH 8.0 | 0.64 µL |
| 100 µM Forward Primer | 0.18 µL |
| 100 µM Reverse Primer | 0.18 µL |

The Forward Primer had the following oligonucleotide sequence:

(SEQ ID NO: 3)
5'- TCA GCA GTT GAA GGG ACA GAT-3'

The Reverse Primer had the following oligonucleotide sequence:

(SEQ ID NO: 4)
5'- CCA GAA CAA TGA ATG GTT AAG G-3'

The template was purchased from ATCC #12228D-5 (*S. Epidermidis* purified DNA). 2.5 µL of template in water were added to each "template" PCR reaction (2 ng per reaction), and 2.5 uL water alone were added to the "no template" PCR reactions.

The following thermal cycling protocol was used on an ABI Step One Plus ThermalCycler:

50° C. for 2 min.

95° C. for 10 min

Followed by 35 cycles of a two step PCR

95° C. for 15 sec.

60° C. for 1 min.

After PCR, the reaction mix was taken directly to a Luminex FLEXMAP 3D instrument at low PMT settings and analyzed for Median Fluorescent Intensity (MFI) values using 100 microspheres per MFI data point.

The following raw MFI results were obtained:

TABLE 1

Raw MFI

| Sample | Region 54 non-specific | Region 25 specific |
|---|---|---|
| template | 4251 | 3854 |
| template | 4350 | 3876 |
| template | 4342 | 3804 |
| template | 4375 | 3870 |
| no template | 4320.5 | 4278.5 |
| no template | 4268 | 4215 |
| no template | 4301 | 4315 |
| no template | 4301.5 | 4237 |

These results were averaged in Table 2:

TABLE 2

| | Average MFI | |
|---|---|---|
| | Region 54 non-specific probe | Region 25 specific probe |
| template (ave) | 4330 | 3851 |
| no template (ave) | 4298 | 4261 |

Figure 3:
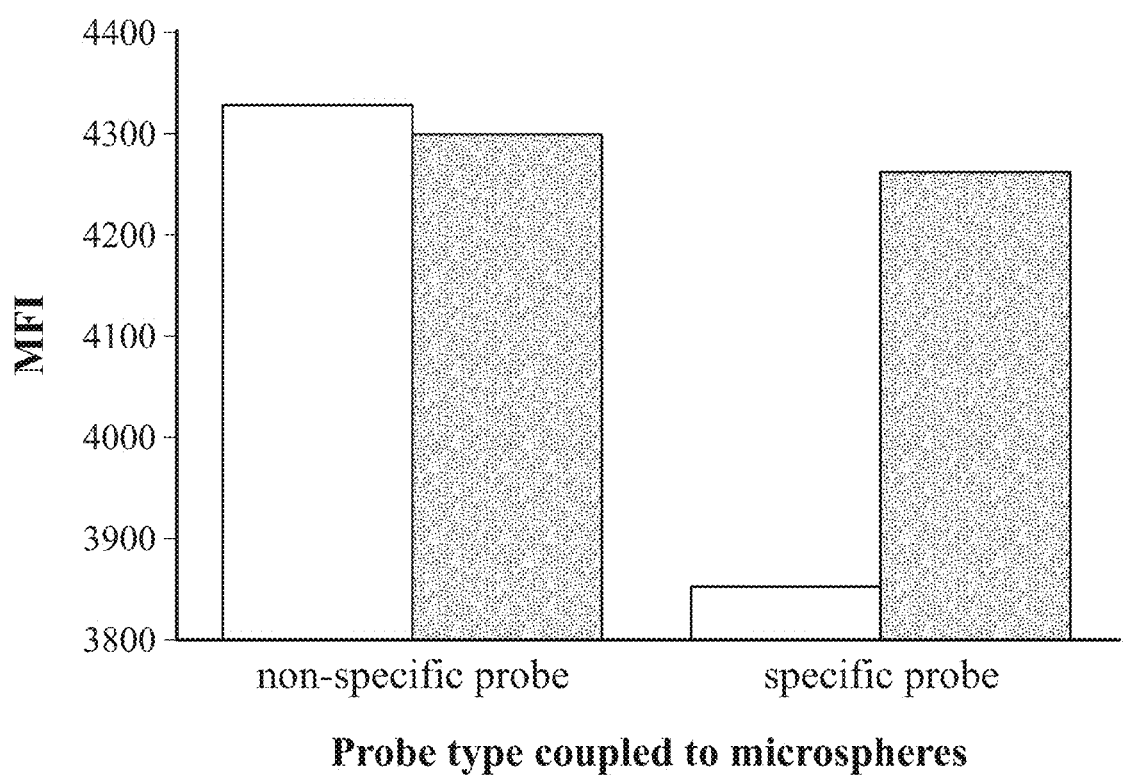
FIG. 3 is a graph showing the MFI for PCR using a target-specific bead set and a control bead set in the presence or absence of template.

A difference of 32 MFI shows for the non-specific probe (i.e. non-hybridizing probe), demonstrating no significant change due to exonuclease activity. For the specific probe, a difference of 410 MFI shows specific exonuclease activity in the presence of template during the PCR reaction. FIG. 3 graphically displays these differences.

All of the compositions and methods disclosed and claimed herein can be made and executed without undue experimentation in light of the present disclosure. While the compositions and methods of this invention have been described in terms of certain embodiments, it will be apparent to those of skill in the art that variations may be applied to the compositions and methods and in the steps or in the sequence of steps of the methods described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. Pat. No. 4,284,412
U.S. Pat. No. 4,498,766
U.S. Pat. No. 4,661,913
U.S. Pat. No. 4,714,682
U.S. Pat. No. 4,767,206
U.S. Pat. No. 4,774,189
U.S. Pat. No. 4,857,451
U.S. Pat. No. 4,942,124
U.S. Pat. No. 4,989,977
U.S. Pat. No. 5,160,974
U.S. Pat. No. 5,210,015
U.S. Pat. No. 5,478,722
U.S. Pat. No. 5,487,972
U.S. Pat. No. 5,538,848
U.S. Pat. No. 5,654,413
U.S. Pat. No. 5,656,493
U.S. Pat. No. 5,716,784
U.S. Pat. No. 5,736,330
U.S. Pat. No. 5,736,330
U.S. Pat. No. 5,736,330
U.S. Pat. No. 5,837,832
U.S. Pat. No. 5,837,860
U.S. Pat. No. 5,981,180
U.S. Pat. No. 5,981,180
U.S. Pat. No. 5,981,180
U.S. Pat. No. 5,981,180
U.S. Pat. No. 5,981,180
U.S. Pat. No. 5,994,056

U.S. Pat. No. 6,030,787
U.S. Pat. No. 6,046,807
U.S. Pat. No. 6,057,107
U.S. Pat. No. 6,057,107
U.S. Pat. No. 6,103,463
U.S. Pat. No. 6,139,800
U.S. Pat. No. 6,174,670
U.S. Pat. No. 6,174,670
U.S. Pat. No. 6,268,222
U.S. Pat. No. 6,322,971,
U.S. Pat. No. 6,366,354
U.S. Pat. No. 6,411,904
U.S. Pat. No. 6,449,562
U.S. Pat. No. 6,449,562
U.S. Pat. No. 6,514,295
U.S. Pat. No. 6,524,793
U.S. Pat. No. 6,524,793
U.S. Pat. No. 6,528,165
U.S. Pat. No. 6,592,822
U.S. Pat. No. 6,939,720
U.S. Pat. No. 7,205,105
U.S. Pat. No. 7,226,737
U.S. Pat. No. 7,226,737
U.S. Pat. No. 7,645,868
U.S. Pat. No. 7,955,802
U.S. Publn. 2005/0191625
U.S. Publn. 2009/0148849
PCT Appln. WO 93/17126
PCT Appln. WO 97/31256
Fodor et al., *Science*, 251:767-773, 1991.
Holmstrom et al., *Anal. Biochem.* 209:278-283, 1993.
Mueller et al., *Current Protocols in Mol. Biol.*; 15:5:1993.
Newton et al., *Nucl. Acids Res.* 21:1155-1162, 1993.
Pease et al., *Proc. Natl. Acad. Sci. USA*, 91:5022-5026, 1994.
Rasmussen et al., *Anal. Biochem*, 198:138-142, 1991.
Running et al., *BioTechniques* 8:276-277, 1990.
Santalucia et al., *Biochemistry*; 38:3468-3477, 1999.

---

The invention claimed is:

1. A method for detecting a target nucleic acid in a sample, comprising:
    (a) contacting the sample with a first target-specific primer complementary to a first region on a first strand of the target nucleic acid, and a target-specific probe complementary to a second region on the first strand of the target nucleic acid downstream of the first region under stringent conditions for hybridization of the target nucleic acid with the first target-specific primer and the target-specific probe, wherein the target-specific probe comprises a tag at its 5' or 3' end and a reporter;
    (b) cleaving the hybridized target-specific probe with a nucleic acid polymerase having exonuclease activity to release the reporter from the tag;
    (c) hybridizing the tag to a complementary anti-tag immobilized on a solid support; and
    (d) detecting the target nucleic acid by detecting a decrease in signal from the reporter on the solid support, wherein the decrease in signal from the reporter is determined by comparison to a reference signal from a reporter on a non-hybridizing probe attached to a solid or to a signal from the reporter on the solid support prior to the cleaving of the hybridized target-specific probe.

2. The method of claim 1, wherein the first target-specific primer and the target-specific probe hybridize to adjacent sequences on the target nucleic acid.

3. The method of claim 1, wherein the first target-specific primer and the target-specific probe hybridize to non-adjacent sequences on the target nucleic acid.

4. The method of claim 1, further comprising extending the first target-specific primer with the nucleic acid polymerase having exonuclease activity.

5. The method of claim 1, further comprising hybridizing the target-specific probe to the anti-tag immobilized on the solid support prior to cleaving the hybridized target-specific probe to release the reporter molecule from the tag; and detecting a signal from the reporter on the solid support.

6. The method of claim 1, wherein the reporter is a biotin or a fluorphore.

7. The method of claim 1, wherein the solid support is an encoded bead.

8. The method of claim 1, wherein the target nucleic acid is a first target nucleic acid, the reporter is a first reporter, the tag is a first tag, the anti-tag is a first anti-tag, the solid support is a first solid support, and the method further comprises:
    (a) contacting the sample with a second target-specific primer complementary to a first region on a first strand of a second target nucleic acid, and a second target-specific probe complementary to a second region on the first strand of the second target nucleic acid downstream of the first region under conditions suitable for hybridization of the second target nucleic acid with the second target-specific primer and the second target-specific probe, wherein the second target-specific probe comprises a second tag at its 5' or 3' end and a second reporter;
    (b) cleaving the second hybridized target-specific probe with the nucleic acid polymerase having exonuclease activity to release the second reporter from the second tag;
    (c) hybridizing the second tag to a complementary second anti-tag immobilized on a second solid support, wherein the first tag is not complementary to the second anti-tag and the second tag is not complementary to the first anti-tag; and
    (c) detecting the second target nucleic acid by detecting a decrease in signal from the second reporter on the second solid support.

9. The method of claim 8, wherein the first solid support and the second solid support are spatially discrete locations on one solid support.

10. The method of claim 8, wherein the first solid support is physically separate from the second solid support.

11. The method of claim 8, wherein the first reporter and the second reporter are the same.

12. The method of claim 8, wherein the first reporter and the second reporter are different.

13. The method of claim 1, further comprising contacting the sample with a second target-specific primer complementary to a region on a second strand of the target nucleic acid.

14. The method of claim 13, further comprising performing multiple polymerase chain reaction cycles.

15. The method of claim 14, wherein the multiple polymerase chain reaction cycles are performed without a wash step to remove free-floating fluorophore between cycles.

16. The method of claim 14, wherein detecting the decrease in signal from the reporter on the solid support comprises detecting the signal before and after performing the multiple polymerase chain reaction cycles.

17. The method of claim 14, wherein detecting the decrease in signal from the reporter on the solid support comprises detecting the signal only after performing the multiple polymerase chain reaction cycles.

18. The method of claim 1, further comprising a linker between the anti-tag and the solid support.

* * * * *